United States Patent [19]

Nagatani et al.

[11] 4,247,620
[45] Jan. 27, 1981

[54] LIGHT-SENSITIVE SILVER HALIDE PHOTOGRAPHIC MATERIAL AND METHOD FOR PROCESSING THE SAME

[75] Inventors: Toshio Nagatani; Kazuo Takahashi; Takeshi Habu, all of Hino, Japan

[73] Assignee: Konishiroku Photo Industry Co., Ltd., Tokyo, Japan

[21] Appl. No.: 49,132

[22] Filed: Jun. 18, 1979

[30] Foreign Application Priority Data

Jun. 23, 1978 [JP] Japan .................. 53-76157

[51] Int. Cl.³ ..................... G03C 1/06; G03C 5/30
[52] U.S. Cl. ........................ 430/264; 430/265;
  430/434; 430/447; 430/564; 430/599; 430/601;
  430/610; 430/612; 430/949
[58] Field of Search ............... 430/607, 610, 949, 599,
  430/601, 564, 569, 631, 264, 265, 434, 447, 612

[56] References Cited

U.S. PATENT DOCUMENTS

| | | | |
|---|---|---|---|
| 2,238,632 | 4/1941 | Dersch et al. | 96/109 |
| 3,951,661 | 4/1976 | Soma et al. | 96/109 |
| 4,013,469 | 3/1977 | Haga et al. | 96/109 |

Primary Examiner—Mary F. Downey
Attorney, Agent, or Firm—Frishauf, Holtz, Goodman & Woodward

[57] ABSTRACT

A light-sensitive silver halide photographic material which comprises a compound represented by general formula [I] shown below:

General formula [I]

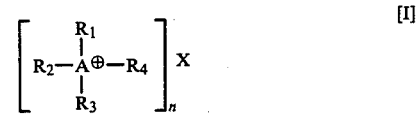

wherein A represents a phosphorus atom, a nitrogen atom or an arsenic atom; $R_1$, $R_2$, $R_3$ and $R_4$ each represent a substituted or unsubstituted aryl group; X represents a persulfate ion, a chlorate ion, a bromate ion, an iodate ion or a metal complex anion; and n is an integer of 1 to 4, and a method for processing the same.

17 Claims, No Drawings

LIGHT-SENSITIVE SILVER HALIDE PHOTOGRAPHIC MATERIAL AND METHOD FOR PROCESSING THE SAME

This invention relates to a light-sensitive silver halide photographic material for the use of high-contrast photography and a method for processing the same. More particularly, this invention relates to a light-sensitive silver halide photographic material which suffers neither sensitization nor desensitization caused by dry pressure in the process for obtaining a dot image by using a general-purpose developing solution and a method for processing the same.

It is desirable that the dot image which is necessary in the field of printing-plate-making has only the maximum density region and the minimum density region, and does not have intermediate density region. Particularly, it is required that the dot image is of such high-contrast that it has a gamma ($\gamma$) value of not less than 10 in the photographic characteristic curve (so-called H-D curve).

In order to obtain such a photographic image, there has usually been used a combination of a high-contrast light-sensitive silver halide photographic material and an alkaline lith type developing solution (also referred to as an infectious developing solution; hereinafter referred to as a lith type developing solution) which develops the former in high-contrast. For instance, a high-contrast image has been obtained by processing, with a lith type developing solution in which developer substantially is hydroquinone only, a high-contrast light-sensitive silver halide photographic material which comprises a chlorobromide emulsion containing a high content of silver chloride (at least not less than 50 mol %) and having an average grain size of about 0.2 to 0.4$\mu$, and a narrow grain size distribution, the greater part of the grains having a crystal face [1,0,0] and the shape of the grains being uniform.

However, according to such a process, the developing solution is extremely unstable due to the low concentration of sulfite ion in the solution.

As a light-sensitive silver halide photographic material which can give a high contrast silver halide image by using a general-purpose developing solution (general black-and-white developing solution) having a high concentration of sulfite ion for the purpose of enhancing the stability of the developing solution, there may be mentioned a light-sensitive silver halide photographic material containing a tetrazolium compound, as described in Japanese Provisional Patent Publication No. Sho 52-18317/1977.

According to such an art, however, a part on a light-sensitive silver halide photographic material becomes black or white by sensitization or by desensitization, when it is locally under pressure or reduced pressure before exposure to light by folding, twist and warp caused at the time of handling of the lith type light-sensitive silver halide photographic material, and by mechanical pressure caused by drawing of a squeezing roller in a camera scanning the light-sensitive silver halide photographic material at the time of camera operation. The so-called sensitization or desensitization caused by dry pressure has frequently occurred to lower the image quality.

When sensitization or desensitization by dry pressure is inhibited by using various inhibiting agents in order to remove the defect, sensitivity is lowered, fog becomes larger and the dot quality is damaged, and thus a dot image with high quality can not be obtained.

Therefore, there has been desired strongly a light-sensitive silver halide photographic material which gives a high-contrast image and in which sensitization or desensitization caused by dry pressure does not occur.

The first object of this invention is to provide a novel light-sensitive silver halide photographic material with which a high-contrast silver image can be obtained.

The second object of this invention is to provide a novel ultrahigh-contrast light-sensitive silver halide photographic material which is suitable for a line image or a dot image, especially suitable for a lithographic material.

The third object of this invention is to provide a novel ultrahigh-contrast light-sensitive silver halide photographic material in which the sensitization or desensitization phenomenum caused by dry pressure does not occur and with which an excellent line or dot image can be obtained.

Another object is to provide a novel ultrahigh-contrast light-sensitive material which can be processed by a general purpose black-and-white developer besides a lith type developer.

A further object of this invention is to provide a method to obtain a ultrahigh-contrast image using a stable developer.

As a result of investigation, the present inventors have found that the objects mentioned above can be accomplished by incorporating a compound represented by general formula [I] mentioned below (hereinafter referred to as "the compound of this invention") in a light-sensitive silver halide photographic material.

General formula [I]:

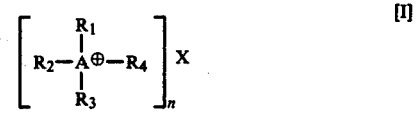

wherein A represents a phosphorous atom, a nitrogen atom or an arsenic atom; $R_1$, $R_2$, $R_3$ and $R_4$ each represent a substituted or unsubstituted aryl group; X represents a persulfite ion, a bromate ion, an iodate ion or a metal complex anion; and n is an integer of 1 to 4.

In general formula [I], A is a penta-valent atom of Va group on Periodic Table, i.e. a phosphorus atom, a nitrogen atom or an arsenic atom. As representative groups for the aryl group may be mentioned a phenyl group, a naphthyl group and the like.

The aryl group may have an optional substituent as occasion demands, and may be mentioned, as preferred substituent, a halogen atom, a nitro group, a hydroxyl group, an acyl group, an alkyl group, an amino group, a carboxylic group, a sulfonyl group, an aryl group (a phenyl group, a naphthyl group), an alkoxy group, an alkoxycarbonyl group, a cyano group and so on.

As the metal complex anion, there may be mentioned an optional one, preferably a complex of at least one metal atom selected from iron, cobalt, nickel, chromium, manganese and copper and an organic polybasic carboxylic acid.

As the organic polybasic carboxylic acid may be mentioned, as a representative one, a compound represented by the following general formula [II].

General formula [II]:

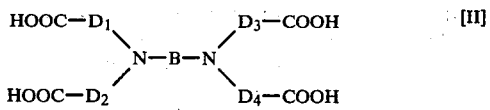

wherein B represents a substituted or unsubstituted alkylene, alkenylene, cycloalkylene, arylene or divalent heterocyclic group, and the alkylene group or the alkenylene group may be connected through an oxygen atom, a sulfur atom or a group >N—R' (in which R' represents a hydrogen atom, an alkyl group having 1 to 4 carbon atoms or a group —D$_5$—COOH); and D$_1$, D$_2$, D$_3$, D$_4$ and D$_5$ each represent an alkylene group having 1 to 4 carbon atoms.

As the substituents of B, i.e., an alkylene group, an alkenylene group, a cycloalkylene group, an arylene group or a divalent heterocyclic group, there may be mentioned an alkyl group having 1 to 4 carbon atoms and a group —D$_5$—COOH. As preferable examples for the divalent heterocyclic group, there may be mentioned a 5 to 7 membered heterocyclic group containing nitrogen, sulfur and/or oxygen atom(s) as a hetero atom.

As the anion there may be mentioned an anion comprising, as a ligand, at least one poly-aminocarboxylic acid selected from ethylenediaminetetraacetic acid, 1,2-propylenediaminetetraacetic acid, trimethylenediaminetetraacetic acid, tetramethylenediaminetetraacetic acid, pentamethylenediaminetetraacetic acid, hexamethylenediaminetetraacetic acid, octamethylenediaminetetraacetic acid, 1,2-cyclopentandiaminetetraacetic acid, transcyclohexane-1,2-diaminetetraacetic acid, cyclohexane-1,3-diaminetetraacetic acid, cyclohexane-1,4-diaminetetraacetic acid, 1,3,5-triaminocyclohexanehexaacetic acid, o-phenylenediaminetetraacetic acid, 2-hydroxytrimethylenediaminetetraacetic acid, ethyl-ether-diaminetetraacetic acid, ethyl-thioether-diaminetetraacetic acid, diethylenetriaminepentaacetic acid, glycol-etherdiaminetetraacetic acid, thioglycol-thioetherdiaminetetraacetic acid, N,N'-dimethyltrimethylenetetraamine-N'',N'',N''',N'''-tetraacetic acid, ethylenediamine-N,N'-diacetic-acid-N,N'-dipropionicacid, ethylenediaminetetrapropionic acid and trimethylenetetraaminehexaacetic acid.

A representative example of above said ligands is ethylenediaminetetraacetic acid.

Next, concrete examples of the compound of this invention (Exemplified compounds) used in this invention will be shown below.

(1) Tetraphenylphosphonium chlorate
(2) Tetraphenylphosphonium persulfate
(3) Tetraphenylphosphonium bromate
(4) p-Ethylphenyltriphenylphosphonium chlorate
(5) Tetraphenylphosphonium iodate
(6) p-Nitrophenyltriphenylphosphonium bromate
(7) p-Cyanophenyltriphenylphosphonium persulfate
(8) p-Methylphenyltriphenylphosphonium chlorate
(9) p-Chlorophenyltriphenylphosphonium chlorate
(10) Tetraphenylarsonium bromate
(11) Tetraphenylammonium persulfate
(12) p-Hydroxyphenyltriphenylphosphonium iodate
(13) p-Nitrophenyltriphenylphosphonium iron (III) ethylenediaminetetraacetate
(14) p-Methylsulfonyltriphenylphosphonium iron (III) ethylenediaminetetraacetate
(15) Tetraphenylphosphonium iron (III) ethylenediaminetetraacetate
(16) p-Hydroxyphenyltriphenylphosphonium iron (III) triethylenediaminetetraacetate
(17) Tetraphenylphosphonium cobalt (III) ethylenediaminetetraacetate
(18) Tetraphenylphosphonium iron (III) 1,2-propylenediaminetetraacetate
(19) Tetraphenylarsonium iron (III) ethylenediaminetetraacetate
(20) Tetraphenylarsonium iron (III) 2-hydroxytrimethylenediaminetetraacetate
(21) Tetraphenylphosphonium iron (III) trimethylenediaminetetraacetate
(22) Tetraphenylphosphonium cobalt (III) pentamethylenediaminetetraacetate
(23) p-Methoxycarbonylphenyltriphenylphosphonium copper (II) ethylenediamine-N,N'-diacetate N,N'-dipropionate
(24) Tetraphenylphosphonium iron (III) tetramethylenediaminetetraacetate
(25) p-Methylsulfonylphenyltriphenylammonium iron (III) trimethylenetetraaminehexaacetate
(26) Tetraphenylphosphonium copper (III) ethylenediaminetetraacetate
(27) Tetraphenylphosphonium iron (III) hexamethylenediaminetetraacetate
(28) Tetraphenylphosphonium manganese (III) ethylenediaminetetraacetate
(29) Tetraphenylphosphonium iron (III) octamethylenediaminetetraacetate
(30) p-Nitrophenyltriphenylphosphonium cobalt (III) ethylenediaminetetraacetate
(31) Tetraphenylphosphonium vanadium (III) ethylenediaminetetraacetate
(32) Tetraphenylphosphonium iron (III) 1,2-cyclopentadiaminetetraacetate
(33) p-Acetylphenyltriphenylphosphonium iron (III) ethylenediamineacetate
(34) Tetraphenylammonium iron (III) o-phenylenediaminetetraacetate
(35) Tetraphenylphosphonium cobalt (III) transcyclohexane-1,2-diaminetetraacetate
(36) p-Carboxyphenyltriphenylphosphonium cobalt (III) ethylenediaminetetraacetate
(37) p-Cyanophenyltriphenylphosphonium iron (III) glycol-etherdiaminetetraacetate
(38) Tetraphenylarsonium iron (III) cyclohexane-1,3-diaminetetraacetate
(39) Biphenyltriphenylphosphonium iron (III) ethylenediaminetetraacetate
(40) Tetraphenylphosphonium nickel (III) ethyl-ether-diaminetetraacetate
(41) Tetraphenylphosphonium iron (III) 1,3,5-triaminocyclohexanehexaacetate
(42) Tetraphenylarsonium cobalt (III) cyclohexane-1,4-diaminetetraacetate
(43) p-Chlorophenyltriphenylphosphonium cobalt (III) ethylenediaminetetraacetate
(44) Tetraphenylarsonium cobalt (III) ethyl-thioether-diaminetetraacetate
(45) p-Aminophenyltriphenylphosphonium iron (III) N,N'-dimethyltrimethylenetetraamine-N'',N'',N''',N'''-tetraacetate
(46) Tetraphenylphosphonium nickel (III) ethylenediamineacetate

(47) Tetraphenylphosphonium iron (III) diethylenetriaminepentaacetate

(48) Tetraphenylphosphonium manganese (III) ethylenediaminetetrapropionate

(49) o-Ethylphenyltriphenylphosphonium chromium (III) ethylenediaminetetraacetate

(50) Tetraphenylphosphonium ferricyanide

(51) Tetraphenylarsonium ferricyanide

As described in U.S. Pat. Nos. 2,238,632, 3,951,661 and so on, the above-mentioned compounds of this invention can easily be synthesized from a halogenide compound having a cation moiety of the compound according to this invention and an alkali metal salt having an anion moiety of the compound according to this invention.

For instance, Exemplified compound (2) mentioned above is obtained by adding dropwise 38 ml. of a 5% aqueous solution of potassium persulfate to 76 ml. of a 5% aqueous solution of tetraphenylphosphonium chloride at 30° C. with stirring, reacting them for 10 minutes and then separating the aqueous phase after completion of the reaction.

Exemplified compound (50) mentioned above is obtained by adding 40 ml. of a 5% aqueous solution of sodium ferricyanide to 38 ml. of a 5% aqueous solution of tetraphenylphosphonium chloride at 35° C. with stirring, reacting them for 15 minutes and then separating the aqueous layer after completion of the reaction.

There have hitherto been known several methods to improve various photographic properties of a light-sensitive silver halide photographic material by incorporating therein a general oxidizing agent or a compound showing an oxidizing action.

The art in connection with these methods has been described in, for example, Japanese Patent Publication Specification No. Sho-47-21755/1972, U.S. Pat. Nos. 3,891,442, 3,847,619, and so on. However, the prior art and the present invention differ from each other in the technical concept, having different concrete means for solving problems and different effects obtained therefrom. For instance, the invention described in Japanese Patent Publication Specification No. Sho-47-21755 and U.S. Pat. No. 3,891,442 relates to a light-sensitive silver halide photographic material which is processed with a hydroquinone developer having a low concentration of sulfite ion, and the same object as in the present invention cannot be achieved in cases where it is processed with a stable general-purpose developing solution as used in the present invention. Further, a light-sensitive material disclosed in U.S. Pat. No. 3,847,619, which is incorporated with a cationic cobalt (III) complex, relates to, as revealed from the specification, a color light-sensitive material and does not show any effect at all for giving high-contrast of not less than 10 in $\gamma$ value of a black-and-white light-sensitive material and for prevention of sensitization or desensitization phenomenum caused by dry pressure, which have been attained by the present invention.

A light-sensitive silver halide photographic material which is incorporated with a quaternary nitrogen compound to improve the photographic properties has been described in British Pat. Nos. 977,804, 1,067,958 and 1,158,263. However, the compound described in British Patent 1,067,958 is different from those of the present invention in the chemical structure. Further, the object to be achieved by the invention of British Pat. No. 1,067,958 relates to acceleration of development or to sensitization and differs from those of this invention.

Similarly, the compound described in British Pat. No. 1,158,263 is a compound having a vinylsulfonyl group and used as a hardener, and the invention of the British Patent is different from this invention in the object and the constitution.

The compound disclosed in U.S. Pat. No. 3,615,510 forms a complex compound by reacting with silver halide. The invention of the U.S. Patent relates to a stabilizing bath and a fixing bath at the time of physical development, and differs entirely from this invention in the object, constitution and effect. The compound described in Japanese Provisional Patent Publication No. Sho-47-41833/1972 relates to an anti-fogging agent; does not show such a high-contrast action as affords a dot image for making of a photographic printing plate; differs in the chemical structure from the compounds to be incorporated in the light-sensitive silver halide photographic material according to this invention; and can not achieve the object of this invention.

Thus, there has not been known, prior to this invention, a light-sensitive silver halide photographic material which have a remarkable ultra-high contrast effect with the compound incorporated in the light-sensitive silver halide photographic material of this invention and which does not suffer sensitization or desensitization caused by dry pressure.

The light-sensitive silver halide photographic material of this invention comprises a support and at least one hydrophilic colloidal layer containing a silver halide emulsion, the latter being coated on the former. The silver halide emulsion layer may be coated directly on a support or may be coated indirectly on a support through a hydrophilic colloidal layer containing no silver halide emulsion. Further, a hydrophilic colloidal layer may further be coated, as a protective layer, on said silver halide emulsion layer. The silver halide emulsion layer may comprise not less than two layers. In such a case, an intermediate layer as a hydrophilic colloidal layer may be located between said silver halide emulsion layer, and an intermediate layer may be located between the silver halide layer and the protective layer. The layer in which the compound of this invention is incorporated is a hydrophilic colloidal layer, preferably a silver halide emulsion layer and/or a hydrophilic colloidal layer adjacent to said silver halide emulsion layer.

The most preferred embodiment of this invention is a light-sensitive silver halide photographic material in which the compound of this invention is incorporated in a silver halide emulsion layer and the hydrophilic colloidal layer comprises gelatin or gelatin derivative.

In order to incorporated the compound of this invention in the hydrophilic colloidal layer, there may be adopted a method where the compound is dissolved in a suitable solvent (e.g., water, methyl alcohol, etc.) and added; and a method where a solution of the compound dissolved in a suitable solvent is added to and dispersed in a hydrophilic colloid matrix of gelatin, a gelatin derivative or the like. At that time, in cases where the dispersion is difficult to be conducted homogeneously, it is preferable to disperse by using an ultra-sonic dispersor or a Manton-Gaulin homogenizer.

The compound according to this invention may preferably be employed in an amount of approximately $1 \times 10^{-5}$ to 10 moles, preferably $1 \times 10^{-4}$ to 1 mole per 1 mole of silver halide contained in the light-sensitive silver halide photographic material.

Not less than two kinds of the compound according to this invention may be used in combination. To use in combination the plurality of the compound according to this invention, they may be incorporated only in the silver halide emulsion layer or may be incorporated additionally in an adjacent layer or in a layer adjacent through an intermediate layer by changing adequately the kinds and the added amounts of the compound of this invention.

As a method for incorporating the compound of this invention in a silver halide emulsion layer, there may be mentioned a method in which the compound is added to a preparative solution of a silver halide emulsion after formation of silver halide grains, before chemical ripening, during chemical ripening, after chemical ripening prior to coating.

The silver halide which is used for the light-sensitive silver halide photographic material according to this invention includes optional silver halides used for a silver halide emulsion, such as silver bromide, silver chlorobromide, silver iodobromide, silver chloroiodobromide, silver chloride and the like. These silver halides may preferably have an average grain size of 0.05 to 0.7μ., more preferably 0.1 to 0.5μ. and preferably not less than 75%, more preferably not less than 80% of the total grains may have grain size of 0.6 to 1.4 times, preferably 0.7 to 1.3 times the average grain size mentioned above. The silver halide may preferably be silver chlorobromide or silver chloroiodobromide containing preferably not less than 50 mole %, more preferably not less than 60 mole % of silver chloride and 0 to 10 mole % of silver iodide.

The silver halide emulsion according to this invention may be sensitized by various conventionally known chemical sensitizers.

Further, the silver halide emulsion used in this invention may be subjected to spectral sensitization by using one or more kinds of sensitizing dyes to be given photo-sensitivity in the desired range of wave length.

In cases where the above-mentioned photo-sensitizing dye, particularly a merocyanine group sensitizing dye is used, not only the effect of photo-sensitization but also the effect of expansion of the development latitude can be obtained.

Moreover, the silver halide emulsion used in this invention may be stabilized by using a chemical stabilizer. Additionally, the silver halide emulsion used in this invention may be incorporated with a stabilizer for latent image such as a sulfur-containing amino compound and a gradation controlling agent such as a cadmium salt, rhodium salt, etc.

While the above-mentioned silver halide emulsion according to this invention and the compound of this invention are incorporated in a hydrophilic colloidal layer (or hydrophilic colloidal layers), the hydrophilic colloid which is used advantageously in this invention is gelatin. A light-sensitive material according to the present invention may also have a hydrophilic colloidal layer containing no silver halide, such as, for example, an antihalation layer, a protective layer, an intermediate layer, a rubbing layer, a filter layer, a backing layer and so on.

The light-sensitive material according to this invention comprises a suitable support for photographic use and the above-mentioned constituting layer coated thereon, which layer contains the above-mentioned silver halide according to this invention and preferably the compound of this invention. In the representative support used in this invention, there may be included, for example, baryta paper, polyethylene-coated paper, polypropylene synthetic paper, glass plate, cellulose acetate, cellulose nitrate, polyester film such as polyethylene terephthalate, polyamide film, polypropylene film, polycarbonate film, polystyrene film and the like. From these supports, an appropriate one is selected in accordance with the purpose of the light-sensitive photographic material to be used.

In the above-mentioned hydrophilic colloid used in this invention, there may be incorporated, as occasion demands, various photographic additives such as gelatin plasticizer, hardener, image stabilizer, ultraviolet absorber, anti-staining agent, pH-adjusting agent, antioxidant, antistatic agent, dye, mordant, fluorescent whitening agent, development-rate-adjusting agent, matting agent and so on, each in an amount which does not damage the effect of this invention.

While the light-sensitive material according to this invention comprises, as mentioned above, a support and at least one hydrophilic colloidal layer coated thereon which contains the compound of this invention, there may desirably be coated a protective layer having an appropriate thickness, preferably 0.1 to 10μ, more preferably 0.5 to 2μ, on the light-sensitive material according to this invention.

Although many of conventionally known lith type light-sensitive materials usually have a protective layer, the protective layer in the present invention has an important role additionally.

Namely, while the protective layer generally is coated only in order to protect the light-sensitive silver halide photographic material from various troubles caused by its contact with other materials, the protective layer in this invention not only protects the above-mentioned light-sensitive silver halide emulsion but also plays an important role for imparting homogeneity in the processing thereof.

The image obtained according to the process of this invention is a high-contrast silver image. Accordingly, this invention can be utilized in various fields in which a high-contrast black-and-white recording is required, and the light-sensitive material obtained in the invention may preferably be applied for use of a light-sensitive material for printing and a light-sensitive material for micro film and so on.

In the present invention, the developer for processing the above-mentioned light-sensitive material may not necessarily be a lith type developer. The light-sensitive material according to this invention can form as high-contrast a silver image as that obtained by processing a lith type light-sensitive material with a lith type developer, even in the presence of sulfite ion of high concentration. In such developer, it is unnecessary to use, as in the lith type developing solution, hydroquinone, low concentration of sulfite ion or a condensation product of carbonylbisulfite and amine, as a buffering agent, (although it may, of course, possibly be used).

The developer used in this invention includes a MQ developer (Methol-hydroquinone developer) and a PQ developer (Phenidone-hydroquinone developer), both of which are general-purpose black-and-white developers and may frequently be used for processing a light-sensitive material having a continuous tone. Particularly, MQ or PQ developer may advantageously be used in this invention due to their excellent stability. Preferably, the developer may show superadditivity; for instance, the developing agent and the development auxiliaries described in The Theory of Photographic Process, 4th ed. page 291-334 (The Macmillan Company, 1977) may advantageously be used for the purpose.

As the developing agent used in this invention, there may be used any of inorganic and organic developing agent. As the representative developing agent there may be mentioned hydroxylamine, hydrazine, catechol, pyrogallol, hydroquinone, chlorohydroquinone, toluhydroquinone, paraaminophenol, p-phenylenediamine and so on.

These developing agent may be used alone or in combination, the latter being preferable. The fact that the effect of this invention is not damaged even when such a sulfite salt as sodium sulfite, potassium sulfite, ammonium sulfite is used, may be mentioned as one of the characteristics of this invention. In the light of the stability, a developer containing larger amount of sulfite is preferred, the concentration of which may preferably be 5-300 g./l., more preferably 15-100 g./l. Further, hydroxylamine and a hydrazide compound may also be used as a preservative. Additionally, it is optional to adjust the pH value of the solution and to bufferize the solution by means of caustic alkali, alkali carbonate or an amine which have been used in general black-and-white developer, and to add an inorganic development-inhibitor such as potassium bromide; an organic development-inhibitor such as benztriazoles; a metal ion sequestering agent such as ethylenediaminetetraacetic acid; a development-rate-regulator such as methanol, ethanol, benzyl alcohol and polyalkylene oxide; a coupler for couples-out-of-emulsion process; a surfactant such as sodium alkylarylsulfonate; a hardener such as glutaraldehyde, formalin and glyoxal; or an ionic-strength-regulator such as sodium sulfate.

The light-sensitive material according to this invention may be processed under various conditions. The processing temperature may preferably be not more than 50° C. and most preferably be around 30° C. While the development may generally be completed within 10 minutes, good results sometimes are obtained by the development within 5 minutes. It is optional to conduct other processing steps than development, such as, for example, water washing, stopping, stabilization, fixing and further to adopt, as the case may be, the steps such as pre-hardening, neutralization and so on, and these steps mentioned above may be omitted as the case may be. Furthermore, these processing may be the so-called development by hand, e.g., dish development, frame development, or a machine development, e.g., roller development, hunger development.

According to a preferred embodiment of this invention, the developer was stable for more than 20 times the period during which the conventional lith type developer is stable, when the stability was investigated by dish development. Particularly, a lith type developer became unusable in several hours, whereas, according to a preferred embodiment of this invention, the developer could stably be used after more than one month had past and the dot quality obtained by using the processing solution was the same as in a freshly prepared developer and thus the developer could be used sufficiently.

As mentioned above, not only the light-sensitive photographic material according to this invention is high-contrast and does not suffer sensitization and desensitization caused by dry pressure but also it is useful for the improvement of other various photographic properties as mentioned below. (1) Aging stability of a coated light-sensitive material is good.
(2) Adhesiveness of a support to a hydrophilic colloidal layer is improved.
(3) Bad influence upon the photographic properties which are caused by inclusion of a fixing solution in a developer during processing is lowered.
(4) Rate of fixing or drying is improved.
(5) Stable processing can be effected.
(6) Adaptability of reduction of image obtained by processing is enhanced.

The present invention will further be explained in detail by way of Comparative examples and Examples which however should not be construed to limit the scope of the present invention.

[EXAMPLE 1]

A silver chlorobromide-gelatin emulsion comprising 90 mole % of silver chloride and 10 mole % of silver bromide and having an average grain size of $0.3\mu$, 85% of the total grains being in a range of grain size of 0.7 to 1.3 times said average grain size, was sensitized chemically by using a sulfur sensitizer and a gold sensitizer. The emulsion was divided into portions, and Comparative compounds and Exemplified compounds of this invention each were added to each portions, as shown in Table 1, and further a coating aid and a hardener were added thereto. Subsequently, the emulsion was coated on a polyethylene terephthalate support so that the coated amounts of silver and gelatin might be 50 mg./100 $cm^2$. and 35 mg./100 $cm^2$., respectively. Further, 15 mg./100 $cm^2$. of gelatin was coated as a protective layer (above thickness was $1.0\mu$) on the silver halide emulsion to prepare specimens.

When the photographic properties were compared, said specimens were wedge-exposed to tungusten light and processed according to the following processing steps.

[Processing steps]

| | |
|---|---|
| Development | 1 minute (30° C.) |
| Fixing | 1 minute |
| Water washing | 1 minute |
| Drying | 40 seconds |

Processing liquids having the following compositions were used.

[Developer]

| | |
|---|---|
| Methol | 5 g. |
| Sodium sulfite anhydrous | 50 g. |
| Hydroquinone | 9 g. |
| Sodium carbonate monohydrate | 50 g. |
| Potassium bromide | 3 g. |
| Sodium ethylenediaminetetraacetate | 0.5 g. |
| 5-Nitroindazole | 60 mg. |

Water was added to make 1 l. and the pH value was adjusted to 10.0.

[Fixer]

| | |
|---|---|
| Ammonium thiosulfate decahydrate | 150 g. |
| Sodium sulfite anhydrous | 10 g. |
| Sodium acetate trihydrate | 15 g. |
| Glacial acetic acid | 17 g. |

Water was added to make 1 l. and the pH value was adjusted to 4.20.

While there were various methods for investigation of dry pressure properties, an investigation was conducted in the present Example with respect to dry pressure properties at the time of representative folding.

The folding test was conducted as follows.

The specimens were allowed to stand for 2 days in an atmosphere of a temperature of 25° C. and a humidity of 30%, and some of the thus treated specimens were folded in 3 seconds at an angle of 45° and a diameter of the folded part of 5 mm. The thus folded specimens were exposed and processed in the same manner as in the former.

The thus obtained photographic properties and dry pressure properties are shown in Table 1.

TABLE 1

|  | Added amount (g/l mol AgX) | Photographic properties γ | fog | **Folding dry pressure properties |
|---|---|---|---|---|
| *Comparative compound (1) | / | 5 | 0.12 | +0.60 |
| *Comparative compound (2) | 3.2 | 10 | 0.04 | +0.55 |
| Exemplified compound 1 | 2.0 | 6 | 0.05 | +0.57 |
| Exemplified compound 4 | 4.5 | 12 | 0.04 | +0.20 |
| Exemplified compound 5 | 4.8 | 11 | 0.04 | +0.15 |
| Exemplified compound 10 | 3.4 | 14 | 0.04 | +0.23 |
| Exemplified compound 13 | 4.3 | 10 | 0.04 | +0.27 |
| Exemplified compound 16 | 3.8 | 15 | 0.04 | +0.26 |
| Exemplified compound 26 | 4.2 | 17 | 0.04 | +0.24 |
| Exemplified compound 36 | 5.5 | 12 | 0.04 | −0.21 |
| Exemplified compound 43 | 3.4 | 13 | 0.04 | +0.31 |
|  | 2.8 | 11 | 0.04 | +0.29 |

*As the Comparative compounds, the following compounds described in Japanese Provisional Patent Publication Specification Nos. Sho-52-18317/1977 and Sho-47-41833/1972 were used.
Comparative compound (1) Tetraphenylphosphonium bichromate
Comparative compound (2) p-Nitrophenyltriphenylphosphonium chloride
**Folding dry pressure properties were represented with +(plus) value in cases where, in the specimen processed to have an image density of 1.0 in the unfolded part, the density of the folded part is higher than that of the unfolded part by the value, and with −(minus) value in cases where the density of the folded part is lower than that of the unfolded part by the value. The larger its absolute value is, the worse the dry pressure property is evaluated to be, and, inversely, the lower the absolute value is, the better the dry pressure property is evaluated to be.

As is clear from the results shown in Table 1, the light-sensitive silver halide photographic material which contains the above-mentioned compound according to this invention can give a high-contrast image and a property extremely low in sensitization or desensitization caused by dry pressure as compared with the Comparative compound.

[Example 2]

A silver chloroiodobromide-gelatin emulsion comprising 70 mole % of silver chloride, 29 mole % of silver bromide and 1 mole % of silver iodide and having an average grain size of 0.4µ, 70% of the total grains being in a range of 0.8 to 1.2 times said average grain size, was sensitized chemically by using a sulfur sensitizer and a gold sensitizer. The emulsion was divided into portions, and Comparative compounds and the compounds of this invention each were added thereto, as shown in Table 2, and a coating aid and a hardener were added further. The emulsions each were coated on a polyethyleneterephthalate support so that the coated amounts of silver and gelatin might be 55 mg./100 cm². and 37 mg./100 cm²., respectively. Further, 20 mg/100 cm². of gelatin was coated as a protective layer (whose thickenss was 1.3µ) on the silver halide emulsion layer to prepare a specimen.

Next, the specimen mentioned above was wedge-exposed to tungusten light and subsequently processed in the same manner as in Example (1).

The thus obtained photographic properties and dry pressure properties are shown in Table 2.

TABLE 2

|  | Added amount (g/l mol AgX) | Photographic properties γ | fog | Folding dry pressure properties |
|---|---|---|---|---|
|  | / | 4 | 0.15 | +0.72 |
| Comparative*** compound (3) | 3.0 | 9 | 0.10 | +0.70 |
| Comparative*** compound (4) | 3.5 | 7 | 0.08 | +0.59 |
| Exemplified compound (8) | 4.7 | 11 | 0.04 | +0.18 |
| Exemplified compound (3) | 3.7 | 13 | 0.04 | +0.26 |
| Exemplified compound (2) | 3.1 | 14 | 0.04 | −0.15 |
| Exemplified compound (15) | 4.5 | 17 | 0.04 | +0.20 |
| Exemplified compound (17) | 4.8 | 14 | 0.04 | +0.23 |
| Exemplified compound (19) | 4.1 | 16 | 0.04 | +0.18 |
| Exemplified compound (28) | 5.1 | 13 | 0.04 | +0.37 |
| Exemplified compound (31) | 4.8 | 12 | 0.04 | +0.29 |
| Exemplified compound (46) | 3.9 | 15 | 0.04 | +0.32 |
| Exemplified compound (50) | 1.8 | 12 | 0.04 | −0.08 |

***As the Comparative compounds, the following compounds described in U.S. Pat. No. 3,891,442 and Japanese Patent Publication Specification No. Sho-47-21755/1972 were used.
Comparative compound (3) Hexaaminecobalt chloride
Comparative compound (4) Sodium bromate Evaluation was conducted in the same manner as in Example (1).

As is clear from the results shown in Table 2, it can be understood that the light-sensitive silver halide photographic material comprising the compound of this invention has a high-contrast photographic property and the compound according to this invention enhances dry pressure property.

[EXAMPLE 3]

In the present Example, the following three kinds of silver halide emulsions were used.

Silver halide emulsion (1): silver chlorobromide comprising 30 mole % of silver chloride and 70 mole % of silver bromide and having an average grain size of 0.50µ, 75% of the total grains having grain sizes of 0.6 to 1.4 times the average grain size.

Silver halide emulsion (2): silver chloroiodobromide comprising 60 mole % of silver chloride 39 mole % of silver bromide and 1 mole % of silver iodide, and having an average grain size of 0.45µ, 60% of the total grains having grain sizes of 0.6 to 1.4 times the average grain size.

Silver halide emulsion (3): silver chlorobromoiodide comprising 72 mole % of silver chloride, 27 mole % of silver bromide and 1 mole % of silver iodide, and having an average grain size of 0.45μ, 80% of the total grains having grain sizes of 0.6 to 1.4 times the average grain size.

The silver halide-gelatin emulsions mentioned above were sensitized chemically by using a sulfur sensitizer and a gold sensitizer.

To each of the three emulsions mentioned above was added Exemplified compound (18) in an amount of 5 g. per 1 mole of silver halide, and a coating aid and a hardener were added thereto.

Subsequently, each of these emulsions was coated on a polyethyleneterephthalate support so that the coated amounts of silver and gelatin might be 53 mg./100 cm². and 32 mg./100 cm²., respectively. Further, 16 mg./100 cm². of gelatin was coated as a protective layer (whose thickness was 1.1μ) on the silver halide emulsion layer to prepare a specimen.

Next, the specimen mentioned above was exposed to light in the same manner as in Example (1), and processed according to the following processing steps.

| [Processing steps] | |
|---|---|
| Development | 45 seconds |
| Fixing | 1 minute |
| Water washing | 1 minute |
| Drying | 1 minute |

The compositions of the procesing solutions used were as follows:

| [Developer] | |
|---|---|
| Phenidone | 0.4 g. |
| Hydroquinone | 15 g. |
| Sodium sulfite anhydrous | 50 g. |
| Sodium carbonate monohydrate | 30 g. |
| Potassium bromide | 4 g. |
| Sodium ethylenediaminetetraacetate | 1 g. |
| Triethanolamine | 10 g. |
| 5-Nitrobenzimidazole | 0.2 g. |

Water was added to make 1 l. and the pH value was adjusted to 10.30.

TABLE 3

| Item for evaluation | Photographic properties | | Folding dry |
|---|---|---|---|
| Silver halide | γ | fog | pressure property |
| Silver halide (1) | 11 | 0.04 | +0.37 |
| Silver halide (2) | 12 | 0.04 | +0.34 |
| Silver halide (3) | 17 | 0.04 | +0.22 |

As is clear from the results shown in Table 3, it is understood that, among the specimens containing the compounds of this invention, the light-sensitive silver halide photographic material comprising silver halide having an average grain size of 0.05 to 0.7μ and a uniform grain size distribution particularly has a high-contrast photographic property and such silver halide enhances dry pressure property.

What is claimed is:

1. A photographic material comprising a lightsensitive silver halide emulsion layer coated on a support which material comprises a compound represented by general formula:

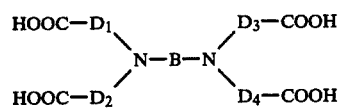

wherein A represents a phosphorus atom, a nitrogen atom or an arsenic atom; $R_1$, $R_2$, $R_3$ and $R_4$ each represent an aryl group or a substituted aryl group wherein the substituent is selected from the group consisting of a halogen atom, a nitro group, a hydroxyl group, an acyl group, an alkyl group, an amino group, a carboxyl group, a sulfonyl group, an aryl group, an alkoxy group, an alkoxy-carbonyl group and a cyano group; X represents a metal complex anion which is a complex of at least one metal selected from iron, cobalt, nickel, chromium, vanadium, manganese and copper, and an organic polybasic carboxylic acid; and n is an integer of 1 to 4.

2. A photographic material according to claim 1 wherein $R_1$, $R_2$, $R_3$ and $R_4$ each represent a substituted or unsubstituted phenyl or naphthyl group.

3. A photographic material according to claim 1 wherein the metal is iron or cobalt.

4. A photographic material according to claim 3 wherein the organic polybasic carboxylic acid is a compound represented by general formula:

$$\begin{array}{c} HOOC-D_1 \diagdown \qquad \diagup D_3-COOH \\ N-B-N \\ HOOC-D_2 \diagup \qquad \diagdown D_4-COOH \end{array}$$

wherein B represents a substituted or unsubstituted alkylene, alkenylene, cycloalkylene, arylene or divalent heterocyclic group, and the alkylene group or the alkenylene group may be connected through an oxygen atom, a sulfur atom or a group >N—R' (in which R' represents a hydrogen atom, an alkyl group having 1 to 4 carbon atoms or a group —$D_5$—COOH); and $D_1$, $D_2$, $D_3$, $D_4$ and $D_5$ each represent an alkylene group having 1 to 4 carbon atoms.

5. A photographic material according to claim 1 or 3 wherein the organic polybasic carboxylic acid is ethylenediaminetetraacetic acid.

6. A photographic material according to claim 1 wherein the compound represented by the general formula [I] is incorporated in the light-sensitive silver halide emulsion layer.

7. A photographic material according to claim 1 or 3 wherein the compound represented by the general formula [I] is incorporated in an amount of $10^{-5}$ to 10 mole per 1 mole of silver halide.

8. A photographic material according to claim 1 or 3 which also contains a protective layer.

9. A photographic material according to claim 8 wherein the thickness of the protective layer is in the range of 0.1 to 10μ.

10. A photographic material according to any one of claims 1, 4 or 5 wherein the light-sensitive silver halide emulsion layer contains silver chlorobromide or chloroiodobromide containing 0 to 1 mole % of silver iodide and not less than 50 mole % of silver chloride and having an average grain size of 0.05 to 0.7μ, at least 75% of the total grains having grain sizes of 0.6 to 1.4 times the average grain size.

11. A photographic material according to claim 10 wherein the compound represented by the general formula [I] is incorporated in an amount of $10^{-5}$ to 10 mole per 1 mole of silver halide; and wherein said photographic material also contains a protective layer between 0.1 and $10\mu$ thick.

12. A photographic material according to claim 11 wherein said organic polybasic carboxylic acid is ethylenediaminetetraacetic acid.

13. A method for processing a photographic material which comprises imagewise exposing a light-sensitive silver halide photographic material and then processing said photographic material in a developer which contains a preservative, said light-sensitive silver halide photographic material comprising a light-sensitive silver halide emulsion layer coated on a support which material comprises a compound represented by the general formula [I]:

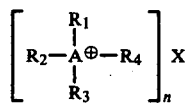

wherein A represents a phosphorus atom, a nitrogen atom or an arsenic atom; $R_1$, $R_2$, $R_3$ and $R_4$ each represent an aryl group or a substituted aryl group wherein the substituent is selected from the group consisting of a halogen atom, a nitro group, a hydroxyl group, an acyl group, an alkyl group, an amino group, a carboxyl group, a sulfonyl group, an aryl group, an alkoxy group, an alkoxy-carbonyl group and a cyano group; X represents a metal complex anion which is a complex of at least one metal selected from iron, cobalt, nickel, chromium, vanadium, manganese and copper, and an organic polybasic carboxylic acid; and n is an integer of 1 to 4.

14. A method for processing according to claim 13 wherein the preservative is a sulfite.

15. A method for processing according to claim 13 wherein the sulfite is contained in an amount of 5 to 300 g./l.

16. A method for processing according to claim 13 wherein the photographic material is processed with a hydroquinone developer.

17. A method for processing according to claim 13 wherein the photographic material is processed with a Phenidone-hydroquinone developer.